United States Patent
Gupta et al.

(10) Patent No.: US 11,103,544 B2
(45) Date of Patent: Aug. 31, 2021

(54) APPLICATION OF HONEY AND BACTERIA IN METHODS OF TREATING SCALP CONDITIONS AND HAIR CONDITIONS

(71) Applicants: Ann and Robert H. Lurie Children's Hospital of Chicago, Chicago, IL (US); Yobee Care, Inc., Chicago, IL (US)

(72) Inventors: Ruchi Gupta, Chicago, IL (US); Tarun Jain, Chicago, IL (US)

(73) Assignees: Ann and Robert H. Lurie Children's Hospital of Chicago, Chicago, IL (US); Yobee Care, Inc., Chicago, IL (US)

( * ) Notice: Subject to any disclaimer, the term of this patent is extended or adjusted under 35 U.S.C. 154(b) by 177 days.

(21) Appl. No.: 16/474,950

(22) PCT Filed: Dec. 28, 2017

(86) PCT No.: PCT/US2017/068765
§ 371 (c)(1),
(2) Date: Jun. 28, 2019

(87) PCT Pub. No.: WO2018/126041
PCT Pub. Date: Jul. 5, 2018

(65) Prior Publication Data
US 2019/0343901 A1    Nov. 14, 2019

Related U.S. Application Data

(60) Provisional application No. 62/440,797, filed on Dec. 30, 2016.

(51) Int. Cl.
| | | |
|---|---|---|
| *A61K 35/744* | (2015.01) | |
| *A61K 35/745* | (2015.01) | |
| *A61P 17/00* | (2006.01) | |
| *A61K 35/747* | (2015.01) | |
| *A61K 9/00* | (2006.01) | |
| *A61K 9/06* | (2006.01) | |
| *A61K 31/12* | (2006.01) | |
| *A61K 31/714* | (2006.01) | |
| *A61K 35/644* | (2015.01) | |
| *A61K 36/9066* | (2006.01) | |
| *A61K 47/10* | (2017.01) | |
| *A61K 47/44* | (2017.01) | |

(52) U.S. Cl.
CPC .......... *A61K 35/747* (2013.01); *A61K 9/0014* (2013.01); *A61K 9/06* (2013.01); *A61K 31/12* (2013.01); *A61K 31/714* (2013.01); *A61K 35/644* (2013.01); *A61K 35/744* (2013.01); *A61K 35/745* (2013.01); *A61K 36/9066* (2013.01); *A61K 47/10* (2013.01); *A61K 47/44* (2013.01); *A61P 17/00* (2018.01)

(58) Field of Classification Search
CPC .... A61K 35/47; A61K 35/744; A61K 35/644; A61K 35/745; A61P 17/00

USPC ....... 424/9.1, 9.2, 93.1, 93.44, 93.45, 234.1, 424/537
See application file for complete search history.

(56) References Cited

U.S. PATENT DOCUMENTS

| | | | |
|---|---|---|---|
| 6,171,604 B1* | 1/2001 | Mousa | A61K 8/988 424/401 |
| 2009/0232785 A1 | 9/2009 | Breton | |
| 2014/0004090 A1* | 1/2014 | Vasquez | A61K 35/747 424/93.45 |
| 2014/0037688 A1* | 2/2014 | Berkes | A61K 35/644 424/244.1 |
| 2016/0243057 A1 | 8/2016 | McWherter et al. | |

FOREIGN PATENT DOCUMENTS

| | | |
|---|---|---|
| WO | 2011109469 A1 | 9/2011 |
| WO | 2012118535 A1 | 9/2012 |

OTHER PUBLICATIONS

Eminence Clear Skin Probiotic Moisturizer. Available for sale as of Dec. 1, 2016. Accessed on Mar. 4, 2020. https://www.amazon.com/gp/product/B005LZT9GU/ref=as_li_tl?ie=UTF8&camp=1789 &creative=390957&creativeASIN=B005LZT9GU&linkCode=as2 &tag=palforwom-20.
International Searching Authority, International Search Report and Written Opinion for application PCT/US2017/068765, dated Mar. 6, 2018.
Suslov A.B. i dr. Inaktivatsiya microoramizmov v srede cverxkriticheskogo CO2. Sverxkriticheskie Fluidy: Teoriya i Praktika. 2008, Tom 3, No. 3 p. 3, paragraph 2. With machine translation.
Epicuren Acidophilus Probiotic Facial Cream. Available for sale as of Dec. 1, 2016. Accessed online at https://www.amazon.co.uk/Epicuren-Acidophilus-Probiotic-Facial-Cream/dp/B000ULF98W on Mar. 4, 2020.

(Continued)

*Primary Examiner* — Rodney P Swartz

(74) *Attorney, Agent, or Firm* — Amin Talati Wasserman LLP; J. Peter Paredes

(57) ABSTRACT

Disclosed are methods and topical compositions for applying bacteria to skin, scalp and hair. The topical compositions include bacteria in a suitable base vehicle comprising honey for applying the bacteria to skin, scalp and hair. The base vehicle may include additional components such as, but not limited to, plant-based products, micro-nutrients, emollients and plant-sourced emulsifiers, and anti-oxidants, among other components. The topical compositions may be utilized in methods for treating and/or preventing skin, scalp, and hair conditions such as, but not limited to, dry skin, dry scalp, dandruff, psoriasis, cradle cap, seborrheic dermatitis, and/or eczema.

23 Claims, No Drawings

(56) References Cited

OTHER PUBLICATIONS

Database WPI. Week 201639. Thomson Scientific, London, BG; AN 2016-30398D & KR 2016 0049812 A (Korean Cosmetics Co Ltd) May 10, 2016.
European Patent Office. Extended European Search Report for application 177889075.2. dated Jun. 15, 2020.

\* cited by examiner

APPLICATION OF HONEY AND BACTERIA IN METHODS OF TREATING SCALP CONDITIONS AND HAIR CONDITIONS

CROSS-REFERENCE TO RELATED PATENT APPLICATIONS

The present application is the U.S. National Stage of International Application PCT/US2017/068765, filed on Dec. 28, 2017, which application claims the benefit of priority under 35 U.S.C. § 119(e) to U.S. Provisional Application No. 62/440,797, filed on Dec. 30, 2016, the content of which is incorporated herein by reference in its entirety.

BACKGROUND

The present invention relates to methods and compositions for introducing bacteria to the skin, scalp, and hair. Specifically, the invention relates to topical compositions that include honey and may be utilized as vehicles for introducing bacteria to the skin, scalp, and hair. In addition to honey, the disclosed topical compositions may include plant-based lipids, micro-nutrients, emollients and plant-sourced emulsifiers, and anti-oxidants, among other components.

The health and character of the skin is an area of concern for a large portion of the population. Beyond the barrier functions the skin provides, it is also responsible for conveying sense information, and—very literally—presenting its wearer to the world. Healthy skin may therefore support one or more of these functions, potentially preventing physical or psychological injury. The skin is a living organ, and should be treated as such. The present invention provides a vehicle to take advantage of this reality, among other things. Billions of dollars are spent every year by people who wish to improve the appearance of their skin, either through their diet, cosmetics, or by some other means.

Presently, many products aimed at improving the health and structure of the skin exist. However, these products are characterized by several limitations. First, and most importantly, these products may not be characterized as being "skin microbiome friendly." The skin is a living part of an intricate web of human cells and microorganisms, and the products presently available are not entirely supportive or compatible with the skin microbiome and pH. Of the multitude of current topical preparations, none are in biological parity with their purported target. Evidence continues to accumulate that nurturing the skin pH and its biome can be beneficial to the skin's condition.

An additional limitation of current topical preparations is their dependence on pharmaceutical agents, synthetic detergents, and the use of skin-irritating preservatives, biocides and solvents. While useful in preparing mass-market skincare products, the inclusion of skin irritating or compromising chemicals in a preparation aimed at improving skin quality represents a contradiction. For example, in order to treat moderate to severe cases of eczema or psoriasis, the current standard of care revolves around the use of corticosteroids, immunosuppressants, ultraviolet radiation, and similar measures. These treatments are not only often expensive, but carry large side-effect profiles, and substantial risk to their recipients. Even in the case of healthy individuals aiming to improve the cosmetic character or general health of their skin, the ingredients in many preparations are at odds with the user's goals.

There is therefore a need for improvement over the shortcomings of skincare products, in the form of a shelf-stable, nutrient-rich solution, which delivers bacteria to the skin. The present invention consists of a vehicle and associated bacterial preparation, aimed at viable application of said bacteria to the skin, scalp, and hair.

SUMMARY

Disclosed are methods and topical compositions for applying bacteria to skin, scalp and hair. The topical compositions include bacteria in a suitable base vehicle comprising honey for applying the bacteria to skin, scalp and hair. In addition to honey, the base vehicle may include components such as, but not limited to, plant-based products, micro-nutrients, emollients and plant-sourced emulsifiers, and anti-oxidants, among other components. The disclosed topical compositions are formulated to be supportive and compatible with the skin microbiome and pH. The topical compositions may be utilized in methods for treating and/or preventing skin, scalp, and hair conditions such as, but not limited to, dry skin, dry scalp, dandruff, psoriasis, cradle cap, seborrheic dermatitis, and/or eczema.

DETAILED DESCRIPTION

The present invention is described herein using several definitions, as set forth below and throughout the application.

Unless otherwise specified or indicated by context, the terms "a", "an", and "the" mean "one or more." For example, "a component" should be interpreted to mean "one or more components."

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

As used herein, a "subject in need thereof" may include a subject in need of skin, scalp, or hair care and/or treatment. A subject in need thereof may include, but is not limited to, a subject having or at risk for developing one or more of dry skin, dry scalp, dandruff, psoriasis, cradle cap, seborrheic dermatitis, and/or eczema.

As used herein, the term "subject" may be used interchangeable with the terms "patient" and "individual." A subject may include a human and/or a non-human animal (e.g., a companion animal such as a dog or a cat).

Vehicle for Applying Bacteria to Skin, Scalp, and Hair

Disclosed are methods and topical compositions for applying bacteria to the skin, scalp, and/or hair. Accordingly, in the methods and topical compositions the bacteria are formulated in a suitable base vehicle comprising honey for applying bacteria to the skin, scalp, and hair as a topical composition. The disclosed topical compositions preferably are formulated to be supportive and compatible with the skin microbiome and pH.

In particular, the base vehicle may include honey as produced by honey bees including, but not limited to, honey produced by any species of the genus *Apis* such as *A. mellifera, A. cerana, A. florea, A. andreniformis, A koschevnikovi*, and *A. dorsata*. The base vehicle may include honey produced by honey bees and collected pollen and nectar from any flowering plant, in particular, honey produced from the pollen and nectar of *Leptospermum scoparium* and its relatives and/or the Mănuka tree or its relatives (i.e., Mănuka honey). Suitable honey for the disclosed topical compositions may include raw honey or processed honey. In some embodiments, honey used in the disclosed compositions has been heat-treated (e.g., via pasteurization) and/or irradiated.

The disclosed topical compositions include a suitable concentration of honey, for example, to prepare a composition for treating and/or preventing skin conditions and/or scalp conditions. In some embodiments, the honey may be present in the disclosed compositions at a concentration of at least about 1%, 2%, 3%, 5%, 7%, 10%, 15%, 20%, 25%, 30%, 35%, 40%, 45%, 50%, 55%, 60%, 65%, 70% (w/w) or higher, or within a range bounded by any of these values (e.g. about 15-60% (w/w) or 20-50% (w/w)).

The disclosed topical compositions include bacteria which may be live bacteria and/or killed bacterial. Killed bacteria for the disclosed compositions may be killed by methods known in the art, including but not limited to heat-treatment, irradiations, and/or chemical treatment. In some embodiments, the bacteria are present in the topical composition at a concentration of at least about $10^4$, $10^5$, $10^6$, $10^7$, $10^8$ colony forming units (CFU)/gram (g) topical composition or higher, or within a concentration range bounded by any of these values (e.g., $10^4$-$10^8$ CFU/g). Where the bacteria are killed bacteria, the concentration of the bacteria added to the composition may be determined prior to killing the bacteria. In other embodiments, the bacteria are present at a concentration of at least about $10^{-8}$, $10^{-7}$, $10^{-6}$, $10^{-5}$, $10^{-4}$ g bacteria/g composition or higher, or within a concentration range bounded by any of these values (e.g., $10^{-7}$-$10^{-8}$ g bacteria/g composition). In other embodiments, the bacteria are present at a concentration of at least about 1%, 2%, 3%, 5%, 7%, 10%, 15%, 20% (w/w) or higher or within a range bounded by any of these values (e.g., at a concentration of 3-10% (w/w)).

In some embodiments, bacteria for the disclosed topical compositions may include bacteria suitable for use in a topical formulation for treating and/or preventing skin conditions and/or scalp conditions. Suitable bacteria for the disclosed compositions may include, but are not limited to bacteria of the genera *Lactobacillus, Bifidobacterium*, or *Streptococcus*, especially *Lactobacillus acidophilus, Lactobacillus plantarum, Lactobacillus rhamnosus, Lactobacillus delbrueckii, Lactobacillus paracasei, Lactobacillus salivarius, Lactobacillus casei, Bifidobacterium lactis, Bifidobacterium longum, Bifidobacterium breve*, and *Streptococcus thermophiles*.

Optionally, the disclosed topical compositions may include additional bacterial species or non-bacterial species that natural occur in honey (e.g. yeasts), products of fermentation (e.g. lactic acid and/or ethanol), peroxides and any other metabolic byproducts of the bacteria listed above, or of those organisms contained in honey, and additional carriers, buffers, emulsifiers, and anti-oxidants.

Additional components for the disclosed topical compositions may include, but are not limited to plant-based products. In some embodiments, the one or more plant-based products are present in the topical composition at a concentration of at least about 5%, 10%, 20%, 30%, 40%, 50%, 55%, 60%, 65%, 70%, 75%, 80%, 85%, 90% or higher, or within a concentration range bounded by any of these values (e.g., 30-90% (w/w), or about 30-70% (w/w), or about 30-50% (w/w)).

Suitable plant-based products for the disclosed topical compositions may include plant-based lipid products. Plant-based lipid products may include plant-based butters (such as shea butter or cocoa butter), plant-based waxes (such as carnauba wax or beeswax), and plant-based oils (such as coconut oil, sunflower oil, or jojoba oil, or fractions thereof).

Suitable plant-based products for the disclosed topical compositions may include plant-based gels, lotions, or other extracts or components. In some embodiments, the disclosed composition comprise a plant-based gel, lotion, or other extract or component from the Aloe vera plant or a plants producing similar substances as the Aloe vera plant.

Additional plant-based components for the disclosed topical compositions may include turmeric (e.g., *Curcuma longa*), turmeric-derived products, or components that are present in turmeric. In some embodiments, the disclosed compositions include turmeric powder and/or components that are present in turmeric such as curcuminoids and essential oils. The disclosed compositions may include components selected from but not limited to curcumin, demethoxycurcumin, and bisdemethoxycurcumin. The disclosed compositions may include components selected from but not limited to turmerone, germacrone, atlantone, and zingiberene. In some embodiments, the disclosed compositions comprise turmeric-derived products, or components that are present in turmeric at a concentration of at least about 0.5%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0% or higher, or within a concentration range bounded by any of these values (e.g., about 0.5-10% (w/w) or about 2.0-6.0% (w/w)).

The disclosed topical compositions may comprise curcuminoids or essential oils (e.g., curcuminoids and essential oils that are present in turmeric (such as curcumin, demethoxycurcumin, and bisdemethoxycurcumin; and turmerone, germacrone, atlantone, and zingiberene)). In some embodiments, the curcuminoids and/or essential oils are present in the composition at a concentration of at least about 0.005%, 0.01%, 0.02%, 0.05%, 0.1%, 0.2%, 0.5% or higher, or within a concentration range bounded by any of these values (e.g., about 0.005-0.5% (w/w) or 0.05-0.5% (w/w)).

Additional plant-based components for the disclosed topical compositions may include, but are not limited to beta-glucans, olive polyphenols, ahi flower oil, carotenoids such as fucoxanthin, ceramides, and fatty acids such as omega-7 oil optionally obtained from sea buckthorn.

The disclosed topical compositions may comprise micronutrient components, including but limited to vitamins. Suitable vitamins may include, but are not limited to vitamin $B_{12}$, vitamin E and/or vitamin $B_3$. In some embodiments, the micronutrient (e.g., vitamin $B_{12}$, vitamin E and/or vitamin $B_3$) is present in the topical composition at a concentration of at least about 0.1%, 0.2%, 0.5%, 1.0%, 1.5%, 2.0%, 2.5%, 3.0%, 3.5%, 4.0%, 4.5%, 5.0%, 5.5%, 6.0% or higher, or within a concentration range bounded by any of these values (e.g., about 0.1-5% (w/w) or about 1-3% (w/w)).

The disclosed topical compositions may comprise a humectant. Suitable humectants may include, but are not limited to glycerin, or other fractions of triglyceride hydrolysis. In some embodiments, the disclosed compositions comprise glycerin (or other fractions of triglyceride hydrolysis) at a concentration of about 1%, 2%, 3%, 5%, 10%, 15%, 20%, 25%, 30% or higher, or within a concentration range bounded by any of these values (e.g., 3-30% (w/w), or about 5-25% (w/w), or about 10-20% (w/w), or about 15% (w/w)).

The disclosed topical compositions may comprise emulsifiers. Suitable emulsifiers may include, but are not limited to, plant-based emulsifiers such as lecithin, especially from *Helianthus annuus*.

The disclosed topical compositions may include anti-oxidants. Suitable anti-oxidants may include, but are not limited to, hydroxytyrosol.

Additional components for the disclosed topical compositions may include, but are not limited to beta-glucans, olive polyphenols, ahi flower oil, carotenoids such as fucoxanthin, ceramides, and fatty acids such as omega-7 oil optionally obtained from sea buckthorn.

The disclosed topical compositions preferably are formulated to be supportive and compatible with the skin microbiome and pH. For example, preferably the disclosed topical compositions have a pH within a range of 6-8. Optionally, the disclosed topical compositions may include a buffering system.

The disclosed topical compositions may be produced by methods known in the art including, but not limited to the following description. This description is not meant to limit future or potential means of production or the claimed subject matter, nor to exhaustively detail all methods currently in use or development. Neither the set of ingredients used in the following description, nor their relative amounts, should be interpreted to limit the claimed subject matter.

A base vehicle comprising honey, shea butter, cocoa butter, and glycerin may be prepared as follows. To an amount of shea butter that consists of 50% of the final formulation by mass, there may be added an amount of softened cocoa butter equal to 25% of the final formulation by mass. After creating a homogenous cream via stirring or blending, an amount of glycerin and honey, equal to 12.5% and 5% of the final formulation by mass, respectively, may be added to the cocoa and shea butter mixture.

A blend containing bacteria from the genera *Lactobacillus*, *Bifidobacterium*, or *Streptococcus*, especially as listed above among, may be dissolved in a solution of distilled water, along with sunflower lecithin, that together are equal to 2.5% of the final formulation by mass. This water-based mixture then may be added to the base vehicle above.

Lastly, sunflower oil and fractioned coconut oil, each in an amount equal to 2.5% of the final formulation by weight, may together be dissolved in the base vehicle above and mixed on low power until integrated to yield a cream-like solution. The resulting product should be refrigerated for 12 to 24 hours. Depending on the crystal structure of the cocoa butter used, applying heat and controlling re-solidification conditions may be necessary to optimize consistency. Preparation may be best conducted slightly above average room temperature, depending on environment and ingredient feedstock. The vehicle and bacterial preparations detailed herein may be adapted for application to other body systems, including for different purposes entirely.

ILLUSTRATIVE EMBODIMENTS

The following embodiments are illustrative and should not be interpreted to limit the scope of the claimed subject matter.

Embodiment 1

A topical composition for skin comprising bacteria and honey.

Embodiment 2

The topical composition of embodiment 1, wherein the bacteria is live bacteria.

Embodiment 3

The topical composition of embodiment 1, wherein the bacteria is killed bacteria.

Embodiment 4

The topical composition of embodiment 3, wherein the killed bacteria is killed by a method selected from heat treatment, irradiation, chemical treatment, and a combination thereof.

Embodiment 5

The topical composition of any of the foregoing embodiments, wherein the bacteria are present in the topical composition at a concentration of at least about $10^4$, $10^5$, $10^6$, $10^7$, $10^8$ colony forming units (CFU)/gram (g) topical composition or higher, or within a concentration range bounded by any of these values (e.g., $10^4$-$10^8$ CFU/g).

Embodiment 6

The topical composition of any of the foregoing embodiments, wherein the honey is selected from Mănuka honey, raw honey, refined honey, and a combination thereof.

Embodiment 7

The topical composition of any of the foregoing embodiments, wherein the honey is present in the topical composition at a concentration of at least about 10%, 15%, 20%, 25%, 30%, 35%, 40%, 45%, 50%, 55%, 60%, 65%, 70% (w/w) or higher, or within a range bounded by any of these values (e.g. about 15-60% (w/w) or 20-50% (w/w)).

Embodiment 8

The topical composition of any of the foregoing embodiments, wherein the bacteria belong to the genus *Lactobacillus*.

Embodiment 9

The topical composition of any of the foregoing embodiments, wherein the bacteria belong to a species selected from *Lactobacillus acidophilus*, *Lactobacillus plantarum*,

*Lactobacillus rhamnosus, Lactobacillus delbruecki, Lactobacillus paracasei, Lactobacillus salivarius*, and *Lactobacillus casei*.

Embodiment 10

The topical composition of any of the foregoing embodiments, wherein the bacteria belong to the genus *Bifidobacterium*.

Embodiment 11

The topical composition of any of the foregoing embodiments, wherein the bacteria belong to a species selected from *Bifidobacterium lactis, Bifidobacterium longum*, and *Bifidobacterium breve*.

Embodiment 12

The topical composition of any of the foregoing embodiments, wherein the bacteria belong to the genus *Streptococcus*.

Embodiment 13

The topical composition of any of the foregoing embodiments, wherein the bacteria are *Streptococcus thermophiles*.

Embodiment 14

The topical composition of any of the foregoing embodiments, further comprising one or more micro-nutrients (e.g., a vitamin such as vitamin $B_{12}$ and/or vitamin E).

Embodiment 15

The topical composition of any of the foregoing embodiments, further comprising vitamin $B_{12}$.

Embodiment 16

The topical composition of embodiment 15, wherein vitamin $B_{12}$ is present in the topical composition at a concentration of at least about 0.1%, 0.2%, 0.5%, 1.0%, 1.5%, 2.0%, 2.5%, 3.0%, 3.5%, 4.0%, 4.5%, 5.0%, 5.5%, 6.0% or higher, or within a concentration range bounded by any of these values (e.g., about 0.1-5% (w/w) or about 1-3% (w/w)).

Embodiment 17

The topical composition of any of the foregoing embodiments, further comprising turmeric and/or derivatives of turmeric such as curcuminoids or essential oils.

Embodiment 18

The topical composition of embodiment 17, wherein turmeric is present in the topical composition at a concentration of at least about 0.5%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0% or higher, or within a concentration range bounded by any of these values (e.g., about 0.5-10% (w/w) or about 2.0-6.0% (w/w)).

Embodiment 19

The topical composition of any of the foregoing embodiments, further comprising curcuminoids or essential oils.

Embodiment 20

The topical composition of embodiment 19, wherein the curcuminoids and/or essential oils are present in the composition at a concentration of at least about 0.005%, 0.01%, 0.02%, 0.05%, 0.1%, 0.2%, 0.5% or higher, or within a concentration range bounded by any of these values (e.g., about 0.005-0.5% (w/w) or 0.05-0.5% (w/w)).

Embodiment 21

The topical composition of any of the foregoing embodiments, further comprising one or more plant lipids, optionally provided by or present in one or more of shea butter, cocoa butter, coconut oil, sunflower oil, and mixtures thereof.

Embodiment 22

The topical composition of embodiment 21, wherein the one or more plant lipids are present in the topical composition at a concentration of at least about 10%, 20%, 30%, 40%, 50%, 55%, 60%, 65%, 70%, 75%, 80%, 85%, 90% or higher, or within a concentration range bounded by any of these values (e.g., 30-90% (w/w), or about 30-70% (w/w), or about 30-50% (w/w)).

Embodiment 23

The topical composition of any of the foregoing embodiments, further comprising one or more of shea butter, cocoa butter, and a mixture thereof.

Embodiment 24

The topical composition of any of the foregoing embodiments, further comprising one or more of coconut oil, sunflower oil, and a mixture thereof.

Embodiment 25

The topical composition of any of the foregoing embodiments, further comprising a humectant.

Embodiment 26

The topical composition of embodiment 25, wherein the humectant is glycerin.

Embodiment 27

The topical composition of claim 26, wherein the glycerin is present in the composition at a concentration of about 1%, 2%, 3%, 5%, 10%, 15%, 20%, 25%, 30% or higher, or within a concentration range bounded by any of these values (e.g., 3-30% (w/w), or about 5-25% (w/w), or about 10-20% (w/w), or about 15% (w/w)).

Embodiment 28

The composition of embodiment 1, further comprising one or more components selected from the group consisting of beta-glucans, hydroxytyrosol, olive polyphenols, ahi flower oil, carotenoids such as fucoxanthin, ceramides, and fatty acids such as omega-7 oil optionally obtained from sea buckthorn.

Embodiment 29

A method of treating a skin condition, the method comprising applying the topical composition of any of the foregoing embodiment to the skin.

Embodiment 30

The method of embodiment 29, wherein the skin condition selected from the group consisting of dry skin, dermatitis, eczema, or a combination thereof.

Embodiment 31

The method of embodiment 29, wherein the skin condition is atopic dermatitis.

Embodiment 32

A method of treating a scalp condition and/or hair condition, the method comprising applying the topical composition of any of embodiments 1-28 to the scalp and/or hair.

Embodiment 33

The method of embodiment 32, wherein the scalp condition and/or hair condition is selected from the group consisting of dry scalp, dandruff, psoriasis, cradle cap, seborrheic dermatitis, eczema, and combinations thereof.

Embodiment 34

The method of embodiment 32, wherein scalp condition is seborrheic dermatitis.

EXAMPLES

The following Example is illustrative and is not intended to limit the scope of the claimed subject matter.

Example 1

Twenty (20) subjects were enrolled to assess a skin cream product and a hair tonic product for comfort and safety. The compositions of the skin cream product and the hair tonic product are as follows:

TABLE 1

| Component | Skin Cream Product | Hair Tonic Product |
| --- | --- | --- |
| Honey | 3 g (~5% (w/w)) | 41 g (~47% (w/w)) |
| Shea Butter | 30 g (~46% (w/w)) | 4 g (~5% (w/w)) |
| Cocoa Butter | 15 g (~23% (w/w)) | — |
| Glycerin | 9 g (~14% (w/w)) | 15 g (~17% (w/w)) |
| Coconut Oil | 1.5 g (~2% (w/w)) | 6 g (~7% (w/w)) |
| Sunflower Oil | 1.5 g (~2% (w/w)) | — |
| Vitamin $B_{12}$ | 0.5 g (~1% (w/w)) | 1 g (~1% (w/w)) |
| Vitamin E | 0.5 g (~1% (w/w)) | 0.5 g (~0.5% (w/w)) |
| Sunflower Lecithin | — | 3 g (~3% (w/w)) |
| Water | — | 14 g (~16% (w/w)) |
| *Lactobacillus* spp. | 4.5 g (~7% (w/w)) | 3 g (~3% (w/w)) |
| Total | 65.5 g | 87.5 g |

The average age of the subjects was 39 (range 10-72) with 10 men and 10 women. Three male and three female subjects also had both skin eczema and dry scalp.

All subjects were instructed to use the skin cream product and the hair tonic product once a day for ten days. The skin cream was to be applied in a thin layer to arms and legs in the morning after a shower. The hair tonic was to be applied to the scalp once a day for seven days. Prior to taking a shower in the morning, a palm-size amount of the hair tonic was to be massaged into the scalp, left in place for about five minutes, and then rinsed in the shower.

A brief questionnaire was conducted on all the subjects after the study. All subjects reported using the product as instructed. No subjects reported any adverse reactions. A questionnaire scale of 1 to 4 was used, with 1 being poor and 4 being excellent. The results are noted in the Table 2.

TABLE 2

| Parameter | Skin Cream Product | Hair Tonic Product |
| --- | --- | --- |
| Ease of Application | 4.0 | 3.95 |
| Adverse Reactions | 0 | 0 |
| Feel on Skin/Scalp | 3.9 | 3.9 |

One of the subjects found the skin cream slightly greasy and gave a rating of 3. Two of the subjects found the hair tonic to be slightly sticky and gave a rating of 3. The 6 subjects who had skin eczema and dry scalp all reported a subjective improvement in the quality of their skin.

Example 2

A hair tonic and a skin cream were prepared with the following components:

Hair Tonic. Vitamin B12: 2%; Turmeric: 4%; Honey: 43%; Base (inactive ingredients): 51%; Bacteria (Heat-killed *Lactobacillus Acidophilus*): 1 million colony forming units per gram of product; and Bacteria (Heat-killed *Lactobacillus Plantarum*): 1 million colony forming units per gram of product.

Skin Cream. Vitamin B12: 2%; Turmeric: 4%; Honey: 30%; Base (inactive ingredients): 64%; Bacteria (Heat-killed *Lactobacillus Acidophilus*): 1 million colony forming units per gram of product; and Bacteria (Heat-killed *Lactobacillus Plantarum*): 1 million colony forming units per gram of product.

Twenty (20) adult and seventeen (17) pediatric subjects with seborrheic dermatitis were enrolled to study the hair tonic, and twenty (20) adult and twenty (20) pediatric subjects with atopic dermatitis were enrolled to study the skin cream. All subjects were instructed to use the skin cream product and the hair tonic product once a day for ten days. The skin cream was to be applied in a thin layer to arms and legs in the morning after a shower. The hair tonic was to be applied to the scalp once a day for ten days. Prior to taking a shower in the morning, a palm-size amount of the hair tonic was to be massaged into the scalp, left in place for about five minutes, and then rinsed in the shower.

A brief questionnaire was conducted on all the subjects after the study. All subjects reported using the product as instructed. No subjects reported any adverse reactions. A questionnaire scale of 1 to 4 was used, with 1 being poor and 4 being excellent. The results are presented in Table 3:

TABLE 3

| Parameter | Skin Cream Product | Hair Tonic Product |
| --- | --- | --- |
| Ease of Application | 4.0 | 3.95 |
| Adverse Reactions | 0 | 0 |
| Feel on Skin/Scalp | 3.9 | 3.9 |
| Improvement of dermatitis | 4.0 | 4.0 |

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

We claim:

1. A method of treating a scalp condition and/or hair condition, the method comprising applying a topical composition comprising honey at 43%, turmeric at 4%, Vitamin B12 at 2%, base inactive ingredients at 51%, and bacteria to the scalp and hair, wherein the bacteria comprise killed *Lactobacillus acidophilus* at 1 million CFUs per gram of topical composition and killed *Lactobacillus plantarum* at 1 million CFUs per gram of topical composition.

2. The method of claim 1, wherein the honey is selected from Manuka honey, raw honey, refined honey, and a combination thereof.

3. The method of claim 1, wherein the scalp condition and/or hair condition is selected from the group consisting of dry scalp, dandruff, psoriasis, cradle cap, seborrheic dermatitis, eczema, and combinations thereof.

4. The method of claim 1, wherein the scalp condition is seborrheic dermatitis.

5. The method of claim 1, wherein the bacteria belong to a genus selected from the group consisting of *Lactobacillus*, *Bifidobacterium*, and *Streptococcus*.

6. The method of claim 1, wherein the bacteria belong to a species selected from *Lactobacillus acidophilus, Lactobacillus plantarum, Lactobacillus rhamnosus, Lactobacillus delbruecki, Lactobacillus paracasei, Lactobacillus salivarius,* and *Lactobacillus casei.*

7. The method of claim 1, wherein the killed *Lactobacillus acidophilus* and the killed *Lactobacillus plantarum* are killed by a method selected from heat treatment, irradiation, chemical treatment, and a combination thereof.

8. The method of claim 1, wherein the topical composition further comprises curcuminoids or essential oils, optionally wherein the curcuminoids or essential oils are present in the composition at a concentration of about 0.005-0.5%.

9. A method of treating a scalp condition and/or hair condition, the method comprising applying a topical composition comprising honey at 30%, turmeric at 4%, Vitamin B12 at 2%, undefined base inactive ingredients at 64%, and bacteria to the scalp and hair, wherein the bacteria comprise killed *Lactobacillus acidophilus* at 1 million CFUs per gram of topical composition and killed *Lactobacillus plantarum* at 1 million CFUs per gram of topical composition.

10. The method of claim 9, wherein the honey is selected from Manuka honey, raw honey, refined honey, and a combination thereof.

11. The method of claim 9, wherein the topical composition further comprises curcuminoids or essential oils, optionally wherein the curcuminoids or essential oils are present in the composition at a concentration of about 0.005-0.5%.

12. The method of claim 9, wherein the bacteria belong to a genus selected from the group consisting of *Lactobacillus*, *Bifidobacterium*, and *Streptococcus*.

13. The method of claim 9, wherein the bacteria comprise killed *Lactobacillus acidophilus*, killed *Lactobacillus bulgaricus*, and killed *Lactobacillus plantarum*.

14. The method of claim 13, wherein the killed *Lactobacillus acidophilus*, the killed *Lactobacillus bulgaricus*, and the killed *Lactobacillus plantarum* are killed by a method selected from heat treatment, irradiation, chemical treatment, and a combination thereof.

15. The method of claim 9, wherein the scalp condition and/or hair condition is selected from the group consisting of dry scalp, dandruff, psoriasis, cradle cap, seborrheic dermatitis, eczema, and combinations thereof.

16. A method of treating a scalp condition and hair condition, the method comprising applying a topical composition comprising honey at 4%, shea butter at 5%, glycerin at 17%, coconut oil at 7%, Vitamin B12 at 1%, Vitamin E at 0.5%, sunflower lecithin at 3%, water at 16%, base inactive ingredients at 43.5%, and bacteria to the scalp and hair, wherein the bacteria comprises *Lactobacillus* spp at 3%.

17. The method of claim 16, wherein the honey is selected from Manuka honey, raw honey, refined honey, and a combination thereof.

18. The method of claim 16, wherein the scalp condition and/or hair condition is selected from the group consisting of dry scalp, dandruff, psoriasis, cradle cap, seborrheic dermatitis, eczema, and combinations thereof.

19. The method of claim 16, wherein the bacteria belong to a genus selected from the group consisting of *Lactobacillus*, *Bifidobacterium*, and *Streptococcus*.

20. The method of claim 1, wherein the bacteria belong to a species selected from *Lactobacillus acidophilus, Lactobacillus plantarum, Lactobacillus rhamnosus, Lactobacillus delbruecki, Lactobacillus paracasei, Lactobacillus salivarius,* and *Lactobacillus casei.*

21. The method of claim 16, wherein the bacteria comprise killed *Lactobacillus acidophilus*, killed *Lactobacillus bulgaricus*, and killed *Lactobacillus plantarum*.

22. The method of claim 16, wherein the killed *Lactobacillus acidophilus* and the killed *Lactobacillus plantarum* are killed by a method selected from heat treatment, irradiation, chemical treatment, and a combination thereof.

23. The method of claim 16, wherein the topical composition further comprises curcuminoids or essential oils, optionally wherein the curcuminoids or essential oils are present in the composition at a concentration of about 0.005-0.5%.

* * * * *